United States Patent [19]

Alscher et al.

[11] Patent Number: 4,718,943

[45] Date of Patent: Jan. 12, 1988

[54] WOOD PRESERVING IMPREGNATING OIL AND USE THEREOF

[75] Inventors: Arnold Alscher, Essen; Gernot Loehnert, Hamminkeln, both of Fed. Rep. of Germany

[73] Assignee: Verkaufsgesellschaft fuer Teererzeugnisse (VfT), Duisburg, Fed. Rep. of Germany

[21] Appl. No.: 873,893

[22] Filed: Jun. 13, 1986

[30] Foreign Application Priority Data

Jun. 25, 1985 [DE] Fed. Rep. of Germany ....... 3522655

[51] Int. Cl.$^4$ .............................................. C09D 5/14
[52] U.S. Cl. .................................. 106/15.05; 427/441
[58] Field of Search .................. 106/15.05; 427/441

[56] References Cited

U.S. PATENT DOCUMENTS 1,469,466 10/1923 Vermeire ............................ 427/441
4,121,995 10/1978 Hsu ..................................... 208/433
4,411,766 10/1983 Garg et al. ......................... 208/409

*Primary Examiner*—Theodore Morris
*Attorney, Agent, or Firm*—Beveridge, DeGrandi & Weilacher

[57] ABSTRACT

A wood preserving impregnating oil with improved leaching, evaporation, and exudation characteristics comprised of:
  10–100 weight % of coal conversion oil,
  0–90 weight % of coal tar impregnating oil,
  0–75 weight % of mineral oil fraction in the boiling range of 200°–400° C.,
  0–60 weight % of alkyl- or cycloalkyl-substituted aromatics with 2 to 4 rings.

6 Claims, No Drawings

WOOD PRESERVING IMPREGNATING OIL AND USE THEREOF

The invention relates to a new wood preserving impregnating oil with improved leaching and evaporation resistance, as well as improved exudation characteristics.

Coal tar impregnating oil is generally recognized as a durable, effective preservative for protecting construction timber, especially in the demanding area of application in construction in contact with earth and water. For these purposes, the impregnating oil is introduced into the wood by appropriate application methods such as pressure or steeping processes.

The action of coal tar oil in this field of application is unsurpassed, because, in addition to its biocidal activity its favorable physical properties, such as its water repelling, elasticity improving, brittleness reducing, strength improving, and surface hardness regulating actions have an advantageous effect.

Heretofore, no other individual wood preservative has produced this combination of properties of wood preserving actions. The almost exclusive employment of coal tar oils for specific wood preservation tasks in applications where there are highly stringent requirements also explains the use thereof, for example, in the case of. wood railroad crossties or poles for overhead electrical lines and posts in earthworks and for constructions in contact with water.

Coal tar oils, however, have the disadvantage that they contain leachable water soluble compounds, even if in only small proportions, that lighter impregnating oil components evaporate, and that oils occasionally exude from properly impregnated wood.

On the one hand, loss of components of the coal tar oil from the impregnated wood, be it by evaporation, leaching, or exudation, also proceeds with loss of the biological and physical action of the oil due to the loss of a portion of the active compounds thereof.

On the other hand, in view of higher occupational hygiene and environmental requirements, reduction of the leachability of the water soluble compounds present to a limited extent in coal tar impregnating oil, of the evaporation of the lighter impregnating oil compounds, and of the "exudation" is required in certain fields of application (Henningsson, Holz als Roh- und Werkstoff, Vol. 41 (1984), 471-175).

Particularly of major concern is the avoidance of exudation of tar oil from impregnated wood, which may occur to a lesser or greater extent depending on the type of wood and impregnation process, because of the contamination of the wood surface.

Therefore, the present invention has as its object the provision of a wood preservative, which possesses the desired range of properties of coal tar with the same economy but is improved with regard to resistance to leaching and evaporation as well as its exudation characteristics.

This object is achieved by a wood preservative composition comprising 10-100 weight % of coal conversion oil,
0-90 weight % of coal tar impregnating oil,
0-75 weight % of mineral oil fraction in the boiling range of 200°-400° C.,
0-60 weight % of alkyl- or cycloalkylsubstituted aromatics with 2 to 4 rings;

and its use for wood improving impregnation by conventional steeping, pressure, or vacuum-pressure impregnation methods.

Coal tar oil impregnating oils are complex mixtures of highly aromatic compounds because of their formation as distillates of coal high temperature tar. They have been extensively studied scientifically, in relation to their activity as such mixtures as well as with regard to the activity of the individual compounds contained in such mixtures. In this way, it was found, among other things, that alkyl aromatics or cycloalkyl aromatics and alicyclic and aliphatic hydrocarbons exhibit a clearly lower wood preserving effect than the aromatic compounds particularly present in coal tar. A method for comparing the biological activity is set forth as a standard test, e.g., the block test in Kolle flasks according to DIN 52 176 or DIN 52 176/EN or DIN 176/EN 73, after leaching or evaporation stress.

These results also agree with the finding that aliphatic and alicyclic hydrocarbons, alkyl aromatics, especially those with longer chains, as well as cycloalkyl aromatics have proven to have insufficient wood preserving action in practice, even when used in mixtures, and have gained importance only as solvents for the introduction of other wood preserving substances.

Analytical studies demonstrate that oily products obtained from coal conversion, e.g., middle oils from coal hydrogenation of coal extraction, contain aromatic compounds, but unlike the higher aromatic compounds present in coal tar, they have much higher proportions of alkyl and cycloalkyl aromatics than a coal tar oil of identical boiling range. This also produces a clearly lower toxic action on basidiomycetes, a type of fungus.

Therefore, laboratory tests in Kolle flasks according to DIN 52 176 with freshly prepared samples corroborates the theoretical considerations that when the fungicidal activity of coal tar impregnating oils is compared with that of coal conversion oils comparable in the boiling range, the coal tar impregnating oils have a clearly higher activity.

It has now been surprisingly found, however, that in evaluating the effectiveness against the fungus class of basidiomycetes after leaching and after evaporation, the decline in biocidal activity in coal tar oils attributed to evaporation and leaching does not occur to a noticeable extent when coal conversion oils are used as impregnating oil.

This is further surprising because evaporation characteristics of the coal conversiion oils comparable to those of coal tar oil could be expected on the basis of the substantially identical boiling range. The discovered properties of coal conversion oil have great significance not only for the practice of wood impregnation but also for the environmental characteristics of the impregnated wood. Thus, not only does the coal conversion oil produce a major improvement; i.e. reduction in the leaching or evaporation characteristics and thereby bring about a relative improvement in wood preservation, but, in addition by the retention of the impregnating agent within the wood, there is also avoided the environmental impact.

Another advantage to the employment of coal conversion oil is the fact that exudation is greatly reduced in comparison with coal tar oil in identical woods and with identical impregnation processes.

The improvement in the evaporation, leaching, and exudation characteristics observed exerts its full effect when the coal conversion oils are combined with coal tar oils and optionally also with petroleum or mineral oil fractions in the boiling range of 200°–400° C. and with alkyl or cycloalkyl aromatic compounds of aromatics with 2 to 4 rings, especially naphthalene and anthracene.

Thus, the employment of coal conversion oils enables improvement in the leaching or evaporation characteristics of coal tar oil formulations in mixtures of said oils accompanied by the advantages of the latter in biocidal effectiveness and of the coal conversion oils in the improvement of evaporation and leaching characteristics.

Coal conversion oils that can be employed in accordance with the invention are middle oil fractions having the boiling range of 200° to 400° C., which are recovered from a process involving direct hydrogenation of coal according to the liquid phase process or are obtained from the extraction of predominantly low ash coal with a preferred coal derived solvent (e.g., anthracene oil) with subsequent hydrogenation. These processes are well known in the art. These coal conversion oils can be employed either alone or in mixtures with alkyl or cycloalkyl aromatic compound and/or coal tar oils wherein the amount of coal conversion oils can be varied from 10 to 100 weight %, that of the coal tar oils in the range of 10 to 90 weight %, that of the mineral oil fraction from 0 to 75 weight %, and that of the alkyl and cycloalkyl aromatics from 10 to 60 weight %.

The invention will be described in further detail in the following illustrative examples.

According to the German Industrial Standard, DIN 52 176, blocks of test wood were impregnated with the impregnating oils defined more precisely hereinafter, and the limiting values of the respective amounts of oil, expressed as Kg/m³ of wood, which permit destruction and which no longer permit destruction, were determined:

(a) immediately after impregnation according to DIN 52 176;

(b) after leaching stress according to DIN 52 76/EN 84;

(c) after evaporation stress according to DIN 76/EN 73.

Examples of impregnating oils used in tests.

1. Coal Conversion Oil 1

Impregnating oil obtained by a process of coal extraction of low ash coal using a coal derived solvent (anthracene oil), and subsequent hydrogenation of the recovered filtered extract in a catalytic hydrocracker at 210 bar and 420° C. The middle oil fraction in the boiling range of 200°–400° C. is separated by distillation for use as the impregnating oil. The density of the employed oil is 0.98 g/cm³, 20° C.

2. Coal Conversion Oil 2

Impregnating oil obtained by a process of direct hydrogenation of coal after the liquid phase process under pressure (100 bar) and at high temperatures (300° C.). The middle oil fraction in the boiling range of 200°–400° C. is separated by distillation for use as the impregnating oil. The density of the employed oil is 0.98 g/cm³ (20° C.).

3. Coal Tar Impregnating Oil

Pure coal tar oil corresponding to the specifications for a wood preserving impregnating oil ("Impregnating Agent BP, WEI-Type B"). Boiling range up to 235° C.: max. 15%; up to 300° C.: min. 30%; up to 355° C.: 65–85%; density: 1.04–1.15; water content: max. 1%, tar acids content: max. 3%.

4. Mixture of Coal Conversion Oil/Coal Tar Impregnating Oil

Mixture of coal conversion oil (2) and coal tar impregnating oil (3) at a 1:1 ratio by weight.

5 Mixture of Coal Conversion Oil/Coal Tar Impregnating Oil/Alkyl Aromatic

Mixture of coal conversion oil (2), coal tar impregnating oil (3), and diisopropylnaphthalene (mixture of isomers) at a 40:40:20 ratio by weight.

The following table sets forth the findings:

| Basidiomycete Test in Kolle Flasks According to DIN 52 176 | | | |
|---|---|---|---|
| | Test Fungi (Mushrooms) | | |
| Impregnating Oil | Coniophora Puteana | Poria Monticola | Lentius lepideus |
| 1. Coal conversion oil (1) | 160 ... 100 | 160 ... 100 | 250 ... 200 |
| 2. Coal conversion oil (2) | 140 ... 100 | 150 ... 120 | 150 ... 200 |
| 3. Coal tar impregnating oil (3) | ... 40 | ... 40 | ... 40 |
| 4. Mixture of coal conversion oil (2) and coal tar impregnating oil (3) | ... 60 | ... 65 | ... 60 |
| 5. Mixture of coal conversion oil (2), coal tar impregnating oil (3), and diisopropylnaphthalene | ... 60 | ... 70 | ... 60 |

| Basidiomycete Test After Leaching Stress (DIN 52 17/EN) | | | |
|---|---|---|---|
| | Test Fungi (Mushrooms) | | |
| Impregnating Oil | Coniophora Puteana | Poria Monticola | Lentius lepideus |
| 1. Coal conversion oil (1) | 200 ... 160 | 250 ... 200 | 250 ... 200 |
| 2. Coal conversion oil (2) | 200 ... 160 | 200 ... 160 | 200 ... 170 |
| 3. Coal tar impregnating oil (3) | 110 ... 80 | 110 ... 80 | 110 ... 80 |
| 4. Mixture of coal conversion oil (2) and coal tar impregnating oil (3) | 110 ... 80 | 100 ... 70 | 100 ... 70 |
| 5. Mixture of coal conversion oil (2), coal tar impregnating oil (3), and diisopropylnaphthalene | 110 ... 80 | 100 ... 70 | 100 ... 70 |

| Basidiomycete Test After Evaporation Stress In Wind Tunnel (DIN 52 17/EN 73) | | | |
|---|---|---|---|
| | Test Fungi (Mushrooms) | | |
| Impregnating Oil | Coniophora Puteana | Poria Monticola | Lentius lepideus |
| 1. Coal conversion oil (1) | 200 ... 160 | 250 ... 200 | 250 ... 200 |

-continued

Basidiomycete Test After Evaporation Stress In Wind Tunnel (DIN 52 17/EN 73).

| Impregnating Oil | Test Fungi (Mushrooms) | | |
|---|---|---|---|
| | Coniophora Puteana | Poria Monticola | Lentius lepideus |
| 2. Coal conversion oil (2) | 200 ... 160 | 200 ... 160 | 200 ... 170 |
| 3. Coal tar impregnating oil (3) | 110 ... 80 | 110 ... 80 | 110 ... 80 |
| 4. Mixture of coal conversion oil (2) and coal tar impregnating oil (3) | 100 ... 70 | 110 ... 80 | 100 ... 70 |
| 5. Mixture of coal conversion oil (2), coal tar impregnating oil (3), and diisopropylnaphthalene | 100 ... 70 | 110 ... 80 | 100 ... 70 |

Further modifications and variations of the invention will be apparent from the foregoing description and are intended to be encompassed by the claims appended hereto.

The German priority application P No. 35 22 655.2 is relied on and incorporated herein by reference.

We claim:

1. A composition comprising:
   10-90 weight % of coal conversion oil,
   10-90 weight % of coal tar impregnating oil,
   0-75 weight % of mineral oil fraction in the boiling range of 200°-400° C.,
   0-60 weight % of alkyl- or cycloalkyl-substituted aromatics with 2 to 4 rings wherein the coal conversion oil is a middle oil fraction having a boiling range of 200° to 400° C. which is recovered from the direct hydrogenation liquid phase process or from coal solvent extraction of low ash coal.

2. The composition according to claim 1 wherein the alkyl and cycloalkyl aromatics are present in the amount of 10 to 60% by weight.

3. The composition according to claim 1 which comprises a mixture of coal conversion oil and coal tar oil in ratio of 1:1 by weight.

4. The composition according to claim 1 which comprises a mixture of coal conversion oil, coal tar oil and diisopropylnaphthalene in a weight ratio of 40:40:20.

5. A process for preserving wood comprising treating wood with a composition comprising:
   10-90 weight % of coal conversion oil,
   10-90 weight % of coal tar impregnating oil,
   0-75 weight % of mineral oil fraction in the boiling range of 200°-400° C.,
   0-60 weight % of alkyl- or cycloalkyl-substituted aromatics with 2 to 4 rings wherein the coal conversion oil is a middle oil fraction having a boiling range of 200° to 400° C. which is recovered from the direct hydrogenation liquid phase process or from coal solvent extraction of low ash coal.

6. A wood product having been treated by contacting with a wood preservative composition comprising:
   10-90 weight % of coal conversion oil,
   10-90 weight % of coal tar impregnating oil,
   0-75 weight % of mineral oil fraction in the boiling range of 200°-400° C.,
   0-60 weight % of alkyl- or cycloalkyl-substituted aromatics with 2 to 4 rings wherein the coal conversion oil is a middle oil fraction having a boiling range of 200° to 400° C. which is from oal solvent extraction of low ash coal.

* * * * *